(12) United States Patent
Bakken et al.

(10) Patent No.: US 6,607,635 B2
(45) Date of Patent: Aug. 19, 2003

(54) PROCESS FOR INCREASING THE SOFTNESS OF BASE WEBS AND PRODUCTS MADE THEREFROM

(75) Inventors: Andrew P. Bakken, Appleton, WI (US); Troy M. Runge, Neenah, WI (US); Kenneth J. Zwick, Neenah, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 0 days.

(21) Appl. No.: 09/997,405

(22) Filed: Nov. 29, 2001

(65) Prior Publication Data

US 2002/0112830 A1 Aug. 22, 2002

Related U.S. Application Data

(63) Continuation-in-part of application No. 09/854,145, filed on May 11, 2001.
(60) Provisional application No. 60/204,083, filed on May 12, 2000.

(51) Int. Cl.[7] ............... D21H 27/38; D21F 11/04
(52) U.S. Cl. .............. 162/123; 162/125; 162/204; 162/202; 162/158; 162/179
(58) Field of Search ................... 162/123, 125, 162/129–130, 208–210, 351–352, 313–314, 202–204, 158, 179

(56) References Cited

U.S. PATENT DOCUMENTS

| | | | |
|---|---|---|---|
| 1,643,147 A | * 9/1927 | Angier | 162/111 |
| 2,934,865 A | * 5/1930 | Pfeiffer | 162/111 X |
| 2,947,058 A | * 8/1960 | Landells et al. | 162/111 X |
| 3,207,657 A | 9/1965 | Wagner et al. | |
| 3,230,136 A | * 1/1966 | Krake | 162/111 |
| 3,290,209 A | * 12/1966 | Ihrman | 162/111 X |
| 3,382,552 A | * 5/1968 | Davis et al. | 162/111 X |
| 3,523,865 A | * 8/1970 | Ihrman | 162/111 |
| 3,866,277 A | * 2/1975 | Hojyo | 26/18.6 |
| 3,879,257 A | 4/1975 | Gentile et al. | |
| 4,529,480 A | 7/1975 | Trokhan | |
| 3,903,342 A | 9/1975 | Roberts, Jr. | |
| 3,906,853 A | * 9/1975 | Wohlfarter | 100/118 |
| 3,994,771 A | 11/1976 | Morgan, Jr. et al. | |
| 4,166,001 A | 8/1979 | Dunning et al. | |
| 4,225,382 A | 9/1980 | Kearney et al. | |
| 4,300,981 A | 11/1981 | Carstens | |
| 4,309,246 A | 1/1982 | Hulit | |
| 4,344,818 A | 8/1982 | Nuttal et al. | |
| 4,637,859 A | 1/1987 | Trokhan | |
| 4,689,119 A | 8/1987 | Weldon | |
| 6,096,169 A | 8/1988 | Hermans et al. | |
| 5,129,988 A | 7/1992 | Farrington, Jr. | |
| 5,230,776 A | 7/1993 | Andersson et al. | |
| 5,494,554 A | 2/1996 | Edwards et al. | |
| 5,529,665 A | 6/1996 | Kaun | |
| 5,562,805 A | 10/1996 | Kamps et al. | |
| 5,656,132 A | 8/1997 | Farrington, Jr. et al. | |
| 5,672,248 A | 9/1997 | Wendt et al. | |
| 5,695,607 A | 12/1997 | Oriaran et al. | |
| 5,759,346 A | 6/1998 | Vinson | |
| 5,851,629 A | 12/1998 | Oriaran et al. | |
| 5,882,479 A | 3/1999 | Oriaran et al. | |
| 5,932,068 A | 8/1999 | Farrington, Jr. et al. | |
| 5,958,185 A | 8/1999 | Vinson et al. | |
| 6,017,418 A | 1/2000 | Oriaran et al. | |
| 6,033,523 A | 3/2000 | Dwiggins et al. | |
| 6,033,761 A | 3/2000 | Dwiggins et al. | |
| 6,068,731 A | 3/2000 | Dwiggins et al. | |
| 6,051,104 A | 4/2000 | Oriaran et al. | |
| 6,103,063 A | 8/2000 | Oriaran et al. | |
| 6,113,740 A | 9/2000 | Oriaran et al. | |
| 6,120,642 A | 9/2000 | Lindsay et al. | |
| 6,143,131 A | 11/2000 | Dwiggins et al. | |
| 6,143,135 A | 11/2000 | Hada et al. | |
| 6,153,053 A | 11/2000 | Harper et al. | |
| 6,183,601 B1 | 2/2001 | Otto et al. | |
| 6,197,154 B1 | 3/2001 | Chen et al. | |
| 6,210,528 B1 | 4/2001 | Wolkowicz | |
| 6,287,426 B1 | 9/2001 | Edwards et al. | |

FOREIGN PATENT DOCUMENTS

| | | |
|---|---|---|
| EP | 0613979 A1 | 9/1994 |
| EP | 0539703 B1 | 3/1997 |
| EP | 0618329 B1 | 8/1999 |
| EP | 0675225 B1 | 2/2000 |
| GB | 2098637 A | 11/1982 |
| WO | WO 9513424 | 5/1995 |
| WO | WO 0008253 A1 | 2/2000 |
| WO | WO 0185438 A2 | 11/2001 |

OTHER PUBLICATIONS

PCT Search Report filed Mar. 27, 2003.

* cited by examiner

*Primary Examiner*—Jose A. Fortuna
(74) *Attorney, Agent, or Firm*—Dority & Manning, P.A.

(57) ABSTRACT

A process for increasing the tactile properties of a base web without adversely affecting the strength of the web is disclosed. In general, the process includes the steps of placing a base web in between a first moving conveyor and a second moving conveyor. The conveyors are then wrapped around a shear inducing roll which creates shear forces that act upon the base web. The shear forces disrupt the web increasing the softness and decreasing the stiffness of the web. The shear inducing roll typically has a relatively small diameter. In some applications, more than one shear inducing roll may be incorporated into the system.

41 Claims, 9 Drawing Sheets

PROCESS FOR INCREASING THE SOFTNESS OF BASE WEBS AND PRODUCTS MADE THEREFROM

RELATED APPLICATIONS

The present application is a continuation-in-part application of U.S. Ser. No. 09/854,145, filed on May 11, 2001, which claims priority to a Provisional Application having U.S. Ser. No. 60/204,083 filed on May 12, 2000.

BACKGROUND OF THE INVENTION

Products made from base webs such as bath tissues, facial tissues, paper towels, industrial wipers, food service wipers, napkins, medical pads, and other similar products are designed to include several important properties. For example, the products should have a soft feel and, for most applications, should be highly absorbent. The products should also have good stretch characteristics and should resist tearing. Further, the products should also have good strength characteristics, should be abrasion resistant, and should not deteriorate in the environment in which they are used.

In the past, many attempts have been made to enhance and increase certain physical properties of such products. Unfortunately, however, when steps are taken to increase one property of these products, other characteristics of the products may be adversely affected. For instance, the softness of nonwoven products, such as various paper products, can be increased by several different methods, such as by selecting a particular fiber type, or by reducing cellulosic fiber bonding within the product. Increasing softness according to one of the above methods, however, may adversely affect the strength of the product. Conversely, steps normally taken to increase the strength of a fibrous web typically have an adverse impact upon the softness, the product. Conversely, steps normally taken to increase the strength of a fibrous web typically have an adverse impact upon the softness, the stiffness or the absorbency of the web.

The present invention is directed to improvements in base webs and to improvements in processes for making the webs in a manner that optimizes the physical properties of the webs. In particular, the present invention is directed to a process for improving the tactile properties, such as softness and stiffness, of base webs without severely diminishing the strength of the webs.

SUMMARY OF THE INVENTION

As stated above, the present invention is directed to further improvements in prior art constructions and methods, which are achieved by providing a process for producing base webs, namely base webs containing pulp fibers. The process includes the steps of first forming a base web. The base web can be made from various fibers and can be constructed in various ways. For instance, the base web can contain pulp fibers and/or staple fibers. Further, the base web can be formed in a wet lay process, an air forming process, or the like.

Once the base web is formed, the web is placed in between a first moving conveyor and a second moving conveyor. The first and second moving conveyors are then guided around a shear inducing roll while the base web is positioned in between the conveyors. The conveyors are sufficiently wrapped around the shear inducing roll and are placed under a sufficient amount of tension so as to create shear forces that act upon the base web. The shear forces disrupt the web increasing the softness and decreasing the stiffness of the web. Of particular advantage, it has been discovered that the softness of the web is increased without substantially reducing the strength of the web. More particularly, it has been discovered that the process shifts the normal strength-softness curve so as to create webs having unique softness and strength properties.

When guided around the shear inducing roll, the base web should have a moisture content of less than about 10%, particularly less than about 5% and more particularly less than about 2%.

The shear inducing roll can rotate or can be a stationary device. For most applications, the shear inducing roll should have a small effective diameter, such as less than about 10 inches, particularly less than about 7 inches and more particularly from about 2 inches to about 6 inches. For most applications, the conveyors should be wrapped around the shear inducing roll at least 40°, and particularly from about 80° to about 270°. Further, the amount of tension placed upon the conveyors when wrapped around the shear inducing roll should be at least 5 pounds per linear inch and particularly from about 10 pounds per linear inch to about 50 pounds per linear inch.

As described above, various types of base webs can be processed according to the present invention. For example, in one embodiment, the base web can be a stratified web including a middle layer positioned between a first outer layer and a second outer layer. In one embodiment, the outer layers can have a tensile strength greater than the middle layer. For example, the outer layers can be made from softwood fibers, while the middle layer can be made from hardwood fibers.

In one embodiment, a weak center layer can be made from cellulose fibers that have been permanently curled, stiffened, or both. For instance, the cellulose fibers can be mercerized fibers or other types of fibers that have been chemically cross-linked. The permanently curled or stiffened fibers will form a center layer having a relatively weak shear strength. The outer layers, on the other hand, can have a shear strength greater than the middle layer. For example, the outer layers can be made from softwood fibers, hardwood fibers, broke, mechanical pulps, or mixtures thereof. The outer layers combined can account for from about 25% to about 75% by weight of the base web.

Base webs processed according to the present invention can have various applications and uses. For instance, the webs can be used and incorporated into bath tissues, facial tissues, paper towels, industrial wipers, food service wipers, napkins, medical pads, diapers, feminine hygiene products, and other similar products.

Other features and aspects of the present invention are discussed in greater detail below.

BRIEF DESCRIPTION OF THE DRAWINGS

A full and enabling disclosure of the present invention, including the best mode thereof to one of ordinary skill in the art, is set forth more particularly in the remainder of the specification, including reference to the accompanying figures in which.

Figure 1:
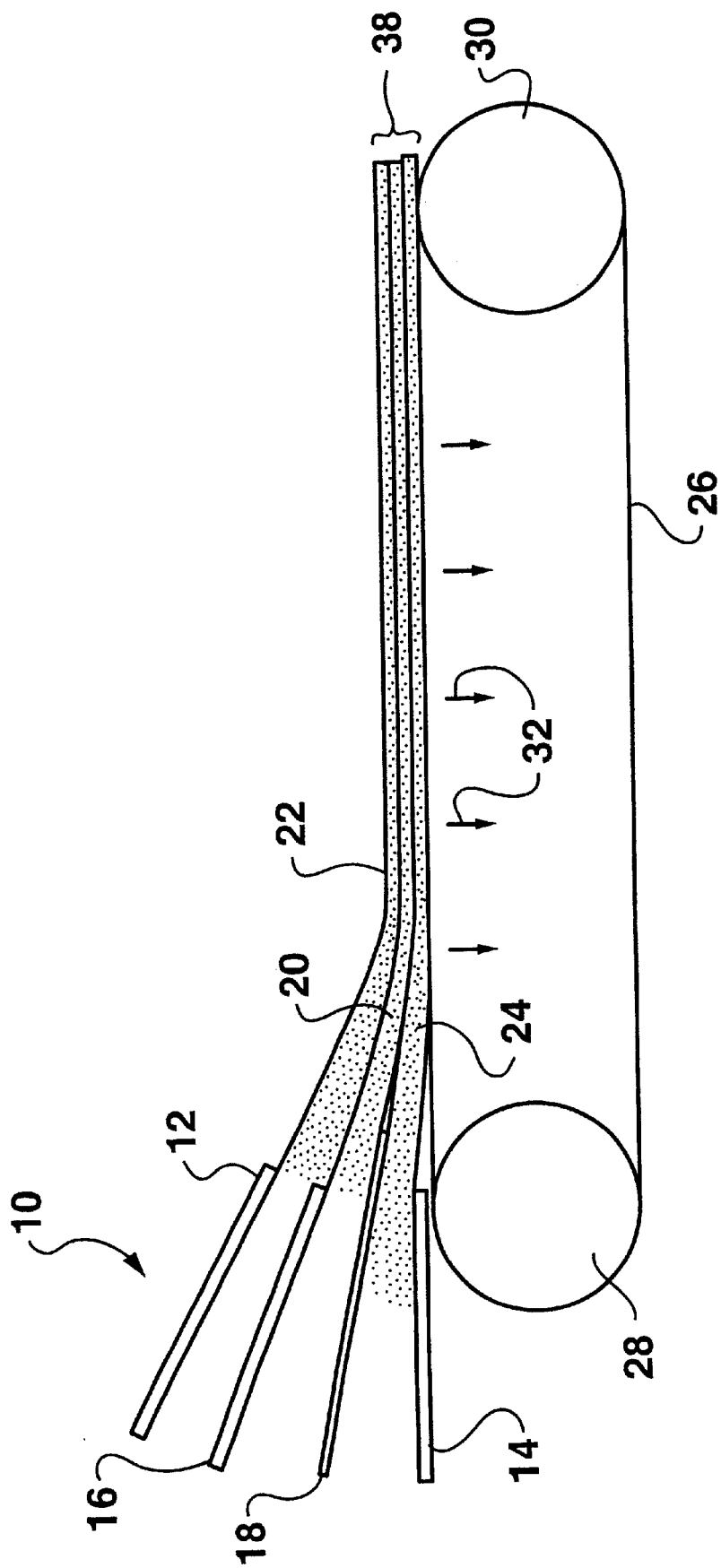
FIG. 1 is a schematic diagram of a fibrous web forming machine illustrating one embodiment for forming a base web having multiple layers in accordance with the present invention.

Repeat use of reference characters in the present specification and drawings is intended to represent same or analogous features or elements of the present invention.

DETAILED DESCRIPTION OF PREFERRED EMBODIMENTS

It is to be understood by one of ordinary skill in the art that the present discussion is a description of exemplary embodiments only, and is not intended as limiting the broader aspects of the present invention, which broader aspects are embodied in the exemplary construction.

In general, the present invention is directed to a process for improving the tactile properties of base webs without a subsequent substantial loss in tensile strength. The present invention is also directed to webs made from the process. In particular, the process of the present invention is well suited to increasing the softness and decreasing the stiffness of base webs, such as webs containing pulp fibers. Further, in some applications, the caliper of a web can be reduced while still gaining all of the above advantages.

Generally speaking, the process of the present invention includes the steps of placing a previously formed base web in between a pair of moving conveyors. As used herein, a conveyor is intended to refer to a flexible sheet, such as a wire, a fabric, a felt, and the like. Once the base web is placed in between the moving conveyors, the conveyors are guided around at least one shear inducing roll. The shear inducing roll can rotate or can be stationary and typically has a small effective diameter, such as less than about 10 inches.

The moving conveyors have a sufficient amount of wrap around the shear inducing roll and are placed under sufficient tension to create shear forces that act upon the base web. Specifically, passing the conveyors over the shear inducing roll causes a speed differential in the conveyors which creates a shearing force that breaks bonds within the web or otherwise disrupts fiber entanglement within the web, where the web is weakest. Through this process, the softness of the web increases while the stiffness of the web is reduced. Unexpectedly, the present inventors have discovered that this softening occurs with substantially less loss of tensile strength than would be expected at the softness levels obtained.

The base web that is processed according to the present invention, in one embodiment, is a stratified web having a relatively weak center layer in comparison to the outer layers. The weak center layer can be made from, for instance, stiffened fibers, such as mercerized fibers, chemically cross-linked fibers, thermally modified fibers, or mixtures thereof. In another embodiment, the weak center layer can contain hardwood fibers, debonded fibers, or synthetic fibers. During the above process, when in-plane shear in imparted to the web, the weaker center layer becomes degraded. The sheet that is formed has 2-ply characteristics, while being made from a single layer. The resulting product is well suited for use in producing facial tissues, bath tissues, and paper towels. For instance, the base web can have a basis weight of less than about 25 lbs per ream for forming tissue products or it can have a basis weight greater than about 15 lbs per ream for forming towel products.

The manner in which the base web of the present invention is formed may vary depending upon the particular application. In one embodiment, the web can contain pulp fibers and can be formed in a wet lay process according to conventional paper making techniques. In a wet lay process, the fiber furnish is combined with water to form an aqueous suspension. The aqueous suspension is spread onto a wire or felt and dried to form the web.

Alternatively, the base web of the present invention can be air formed. In this embodiment, air is used to transport the fibers and form a web. Air forming processes are typically capable of processing longer fibers than most wet lay processes, which may provide an advantage in some applications.

Figure 2:
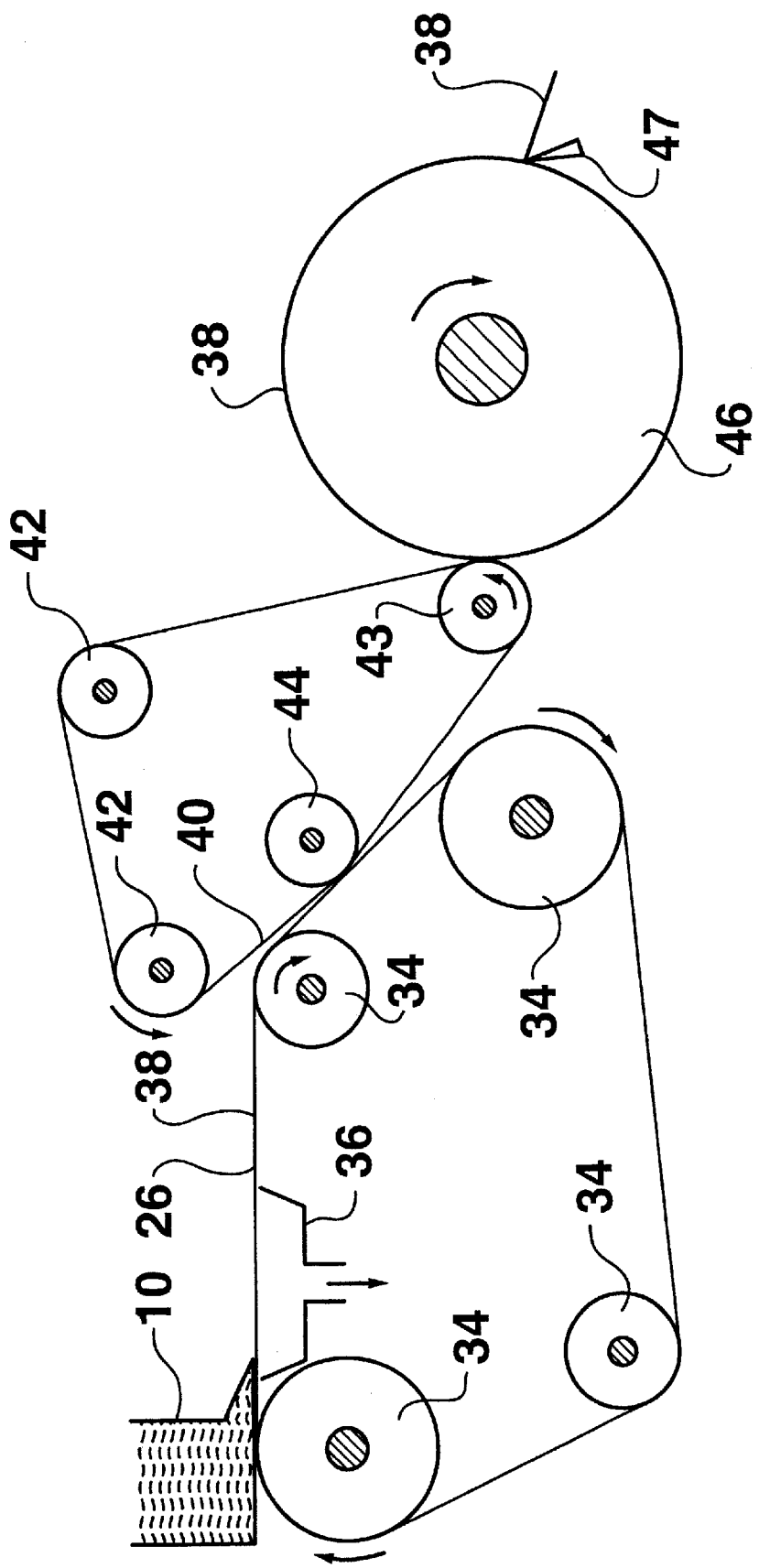
FIG. 2 is a schematic diagram of a fibrous web forming machine that crepes one side of the web.

Referring to FIG. 2, one embodiment of a process for producing a base web that may be used in accordance with the present invention is illustrated. The process illustrated in the figure depicts a wet lay process, although, as described above, other techniques for forming the base web of the present invention may be used.

As shown in FIG. 2, the web forming system includes a headbox 10 for receiving an aqueous suspension of fibers. Headbox 10 spreads the aqueous suspension of fibers onto a forming fabric 26 that is supported and driven be a plurality of guide rolls 34. A vacuum box 36 is disposed beneath forming fabric 26 and is adapted to remove water from the fiber furnish to assist in forming a web.

From forming fabric 26, a formed web 38 is transferred to a second fabric 40, which may be either a wire or a felt. Fabric 40 is supported for movement around a continuous path by a plurality of guide rolls 42. Also included is a pick up roll 44 designed to facilitate transfer of web 38 from fabric 26 to fabric 40. The speed at which fabric 40 can be driven is approximately the same speed at which fabric 26 is driven so that movement of web 38 through the system is consistent. Alternatively, the two fabrics can be run at different speeds, such as in a rush transfer process, in order to increase the bulk of the webs or for some other purpose.

From fabric 40, web 38, in this embodiment, is pressed onto the surface of a rotatable heated dryer drum 46, such as a Yankee dryer, by a press roll 43. Web 38 is lightly pressed into engagement with the surface of dryer drum 46 to which it adheres, due to its moisture content and its preference for the smoother of the two surfaces. As web 38 is carried through a portion of the rotational path of the dryer surface, heat is imparted to the web causing most of the moisture contained within the web to be evaporated.

Web 38 is then removed from dryer drum 46 by a creping blade 47. Creping web 38 as it is formed reduces internal bonding within the web and increases softness.

In an alternative embodiment, instead of wet pressing the base web 38 onto a dryer drum and creping the web, the web can be through air dried. A through air dryer accomplishes the removal of moisture from the base web by passing air through the web without applying any mechanical pressure.

Figure 3:
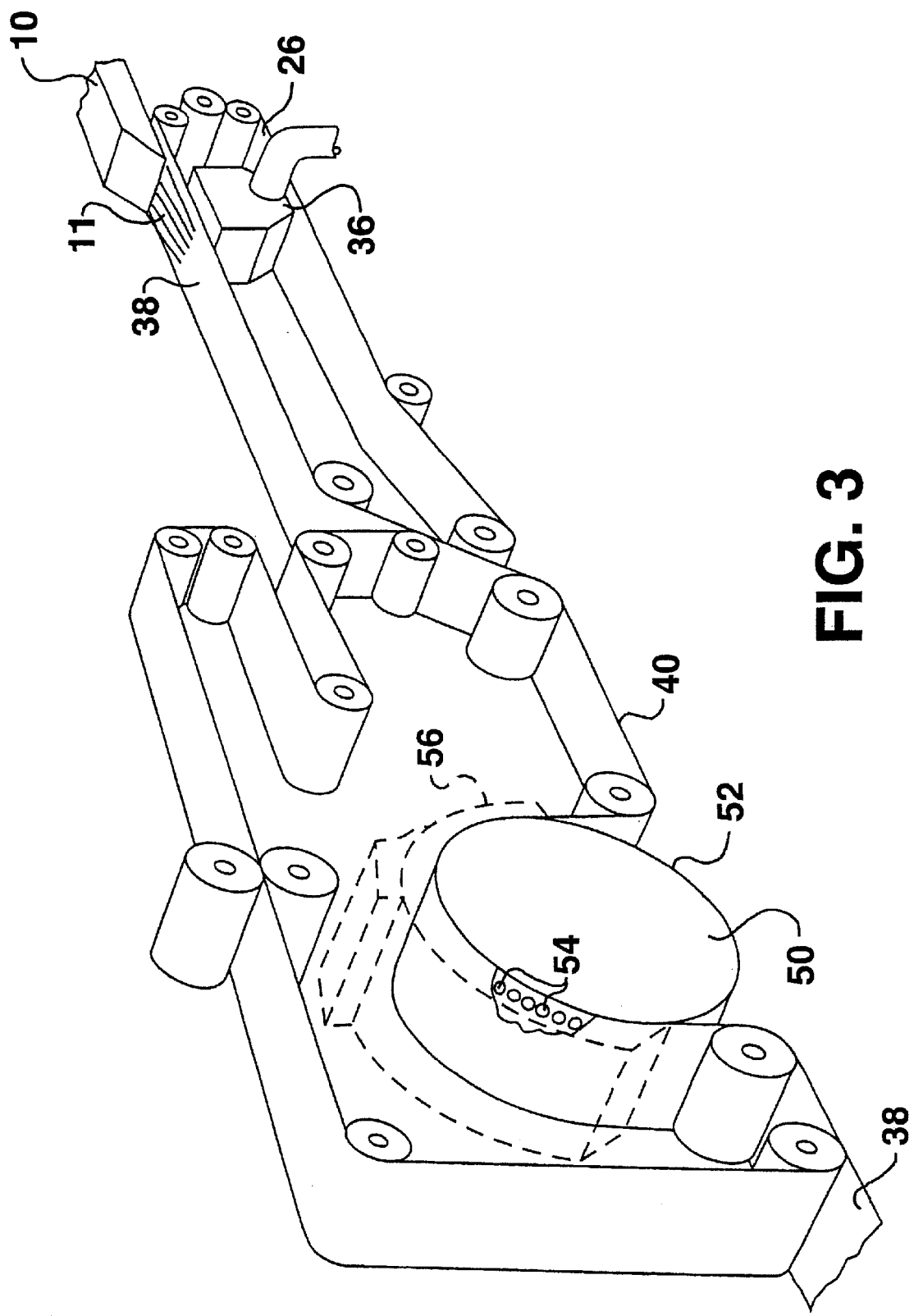
FIG. 3 is a perspective view with cut away portions of a fibrous web forming machine that includes a through air dryer for removing moisture from the web.

For example, referring to FIG. 3, an alternative embodiment for forming a base web for use in the process of the present invention containing a through air dryer is illustrated. As shown, a dilute aqueous suspension of fibers is supplied by a headbox 10 and deposited via a sluice 11 in uniform dispersion onto a forming fabric 26 in order to form a base web 38.

Once deposited onto the forming fabric 26, water is removed from the web 38 by combinations of gravity, centrifugal force and vacuum suction depending upon the forming configuration. As shown in this embodiment, and similar to FIG. 2, a vacuum box 36 can be disposed beneath the forming fabric 26 for removing water and facilitating formation of the web 38.

From the forming fabric 26, the base web 38 is then transferred to a second fabric 40. The second fabric 40 carries the web through a through air drying apparatus 50. The through air drying apparatus 50 dries the base web 38 without applying a compressive force in order to maximize bulk. For example, as shown in FIG. 3, the through air drying apparatus 50 includes an outer rotatable cylinder 52 with perforations 54 in combination with an outer hood 56. Specifically, the fabric 40 carries the web 38 over the upper portion of the through air dryer outer cylinder 52. Heated air is drawn through perforations 54 which contacts the web 38 and removes moisture. In one embodiment, the temperature of the heated air forced through the perforations 54 can be from about 170° F. to about 500° F.

Figure 4:
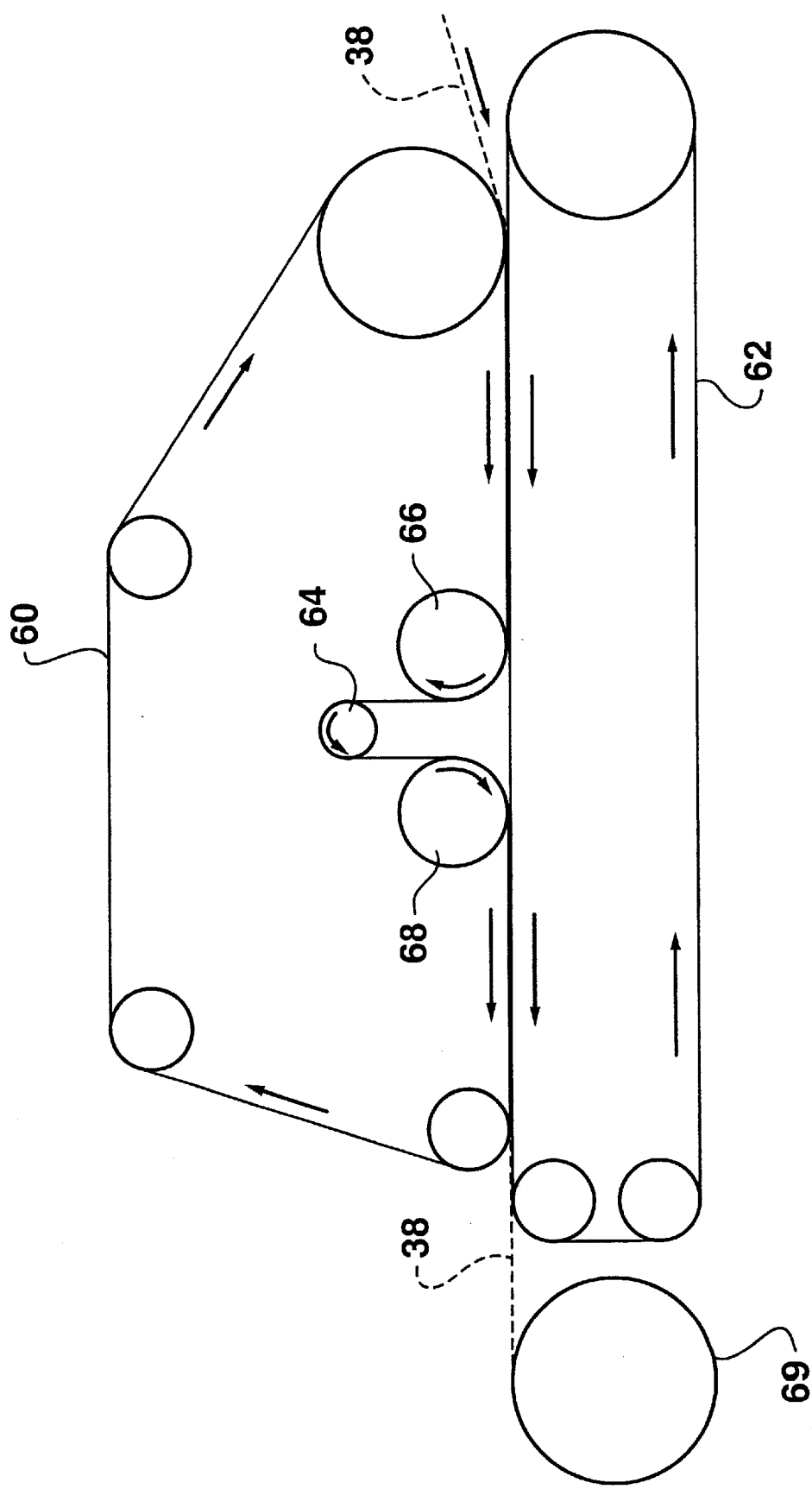
FIG. 4 is a schematic diagram of one embodiment for a process for improving the tactile properties of a formed base web in accordance with the present invention.

After the base web 38 is formed, such as through one of the processes illustrated in FIGS. 2 and 3 or any other suitable process, the web is placed in between a pair of moving conveyors and pressed around a shear inducing roll in accordance with the present invention. For instance, one embodiment of a process for improving the tactile properties of a base web in accordance with the present invention is illustrated in FIG. 4. As shown, the base web 38 is supplied in between a first moving conveyor 60 and a second moving conveyor 62. The speed at which the conveyors 60 and 62 are moving is generally not critical to the present invention. For most commercial applications, the conveyors can be moving at a speed of from about 1,000 feet per minute to about 6,000 feet per minute.

Once positioned in between the first conveyor 60 and the second conveyor 62, the base web and the conveyors are guided around a shear inducing roll 64 by a pair of support rolls 66 and 68. Generally, conveyors 60 and 62 will be traveling at about equal speeds.

In accordance with the present invention, the conveyors 60 and 62 are placed under tension and are wrapped around the shear inducing roll 64 in amounts sufficient to create shear forces that act upon the base web 38. In order to act sufficiently upon the base web between them, conveyors 60 and 62 must be constructed in such a manner so as to impart the necessary shear forces. That is, the conveyors 60 and 62 must have sufficient coefficient of friction so as to act upon the base web surface in contact with either conveyor. Thickness of the conveyors may also play a part in ensuring the ability of the conveyors to impart sufficient shear forces to the web when the conveyors are wrapped around the shear inducing roll with the web between them.

In particular, when the conveyors are passed over the shear inducing roll, a surface speed differential between the surfaces of the web develops due to the difference in path length of the two conveyors around the shear inducing roll. This difference in surface speed creates shear forces which act upon the base web. The shear force breaks bonds within the web where the web is weakest which subsequently increases the softness and decreases the stiffness of the web. Further, the present inventors have discovered that these improvements are realized without a significant decrease in tensile strength as normally occurs in other processes designed to increase softness.

When fed around the shear inducing roll 64, base web 38 should generally have a low moisture content. For example, the base web 38 should have a moisture content of less than about 10% by weight, particularly less than about 5% by weight, and more particularly less than about 2% by weight.

As shown in FIG. 4, the shear inducing roll 64 can be a rotating roll having a relatively small diameter. In other embodiments, however, the shear inducing roll can be a stationary roll. The effective diameter of the shear inducing roll, for most applications, should be less than about 10 inches, particularly less than about 7 inches and more particularly from about 2 inches to about 6 inches.

The amount that conveyors 60 and 62 are wrapped around the shear inducing roll 64 can vary depending upon the particular application and the amount of shear that is desired to be exerted on the web. For most applications, however, the conveyors should be wrapped around the shear inducing roll in an amount from about 40° to about 270°, particularly from about 80° to about 200°, and more particularly from about 100° to about 180°. In the embodiment illustrated in FIG. 4, the amount of wrap placed around the shear inducing roll can be adjusted by adjusting the position of either the shear inducing roll 64 or the support rolls 66 and 68. For instance, by moving the shear inducing roll 64 down closer to the support rolls 66 and 68, the conveyors will wrap around the shear inducing roll 64 a lesser extent.

As described above, besides the amount of wrap that is placed around the shear inducing roll, the amount of tension placed upon the conveyors 60 and 62 also has an impact on the amount of shear that is exerted on the base web 38. The amount of tension placed upon the conveyors will depend upon the particular application. For most applications, however, the conveyors 60 and 62 should be placed under tension in an amount from about 5 pounds per linear inch to about 90 pounds per linear inch, particularly from about 10 pounds per linear inch to about 50 pounds per linear inch, and more particularly from about 30 pounds per linear inch to about 40 pounds per linear inch.

As described above, when the conveyors 60 and 62 are wrapped around the shear inducing roll 64 under a sufficient amount of tension, a surface speed differential develops between the two surfaces of the web that creates the shear forces. For most applications, the path length differential between the two conveyors should be from about 0.5% to about 5%, and particularly from about 1% to about 3%.

After the base web 38 has been guided around the shear inducing roll 64, the web can be further processed as desired. In one embodiment, as shown in FIG. 4, the web can be collected onto a reel 69 for later packaging.

During this process, the tactile properties of the base web can be greatly enhanced, without seriously affecting the strength of the web. Further, in some applications, it has been discovered that the caliper of the web can be dramatically reduced. Caliper reduction without adversely affecting other properties of the web is beneficial in that more material can be placed upon reel 69, which provides various processing benefits. The amount of caliper reduction for a given base web will depend upon the application. In general, the caliper of a sheet is reduced by the pressure (P) applied to it by the tension (T) of the fabrics and the radius (R) of the roll, governed by the equation P=T/R.

The amount of caliper reduction achieved can be controlled by adjusting numerous variables. The number of shear inducing rolls, the radius of the rolls, dwell time within the nip, nip pressure, conveyor type and base sheet structure all have an impact on the amount of caliper the process can remove. Percent caliper reduction can increase with an increase in dwell time, number of rolls, nip pressure, and fabric mesh. Dwell time can be affected by the secondary variables of speed and rap angle. Nip pressure can be varied by the secondary variables of fabric tension and roll diameter. Fabric mesh can be varied by using fabrics of differing knuckle surfaces. Thus far, it has been discovered that the caliper of a base web can be decreased up to as much as 75%, and particularly from about 20% to about 70%.

Figure 5:
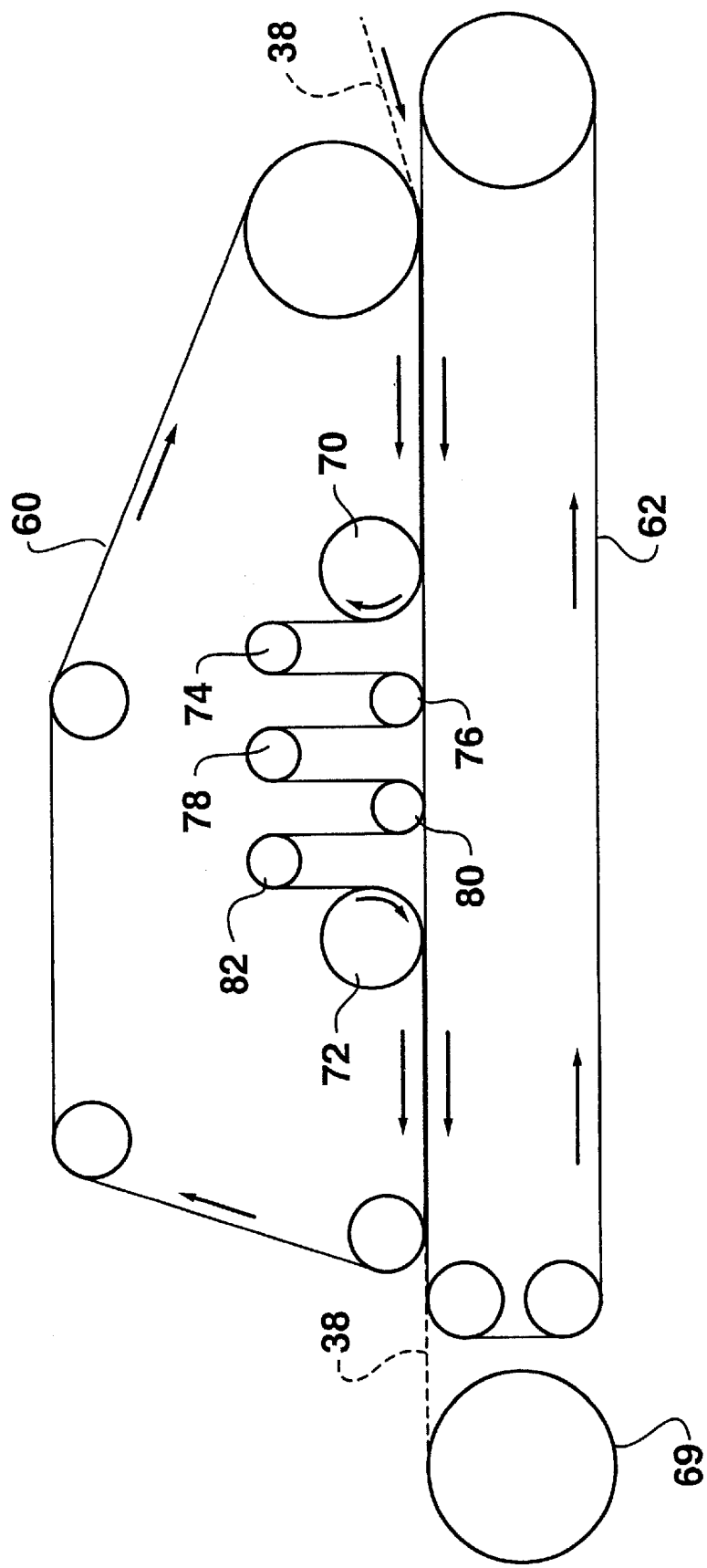
FIG. 5 is a schematic diagram of an alternative embodiment of a process for improving the tactile properties of a formed base web made in accordance with the present invention.

In the embodiment illustrated in FIG. 4, the system includes a single shear inducing roll 64. In other embodiments, however, more shear inducing rolls can be used. For instance, in other embodiments, the conveyors can be wrapped around two shear inducing rolls, three shear inducing rolls, and even up to ten shear inducing rolls. Referring to FIG. 5, an alternative embodiment of the present invention is illustrated that includes five shear inducing rolls.

As shown, the base web 38 is fed between the first conveyor 60 and the second conveyor 62 and is then wrapped around support rolls 70 and 72 and shear inducing rolls 74, 76, 78, 80, and 82. In general, using more shear inducing rolls can create more shear that is exerted on the base web. Although the shear inducing rolls are illustrated in the figures as having equal diameters, alternative embodiments may be desired with shear inducing rolls having diameters which are not equal to each other.

Figure 6:
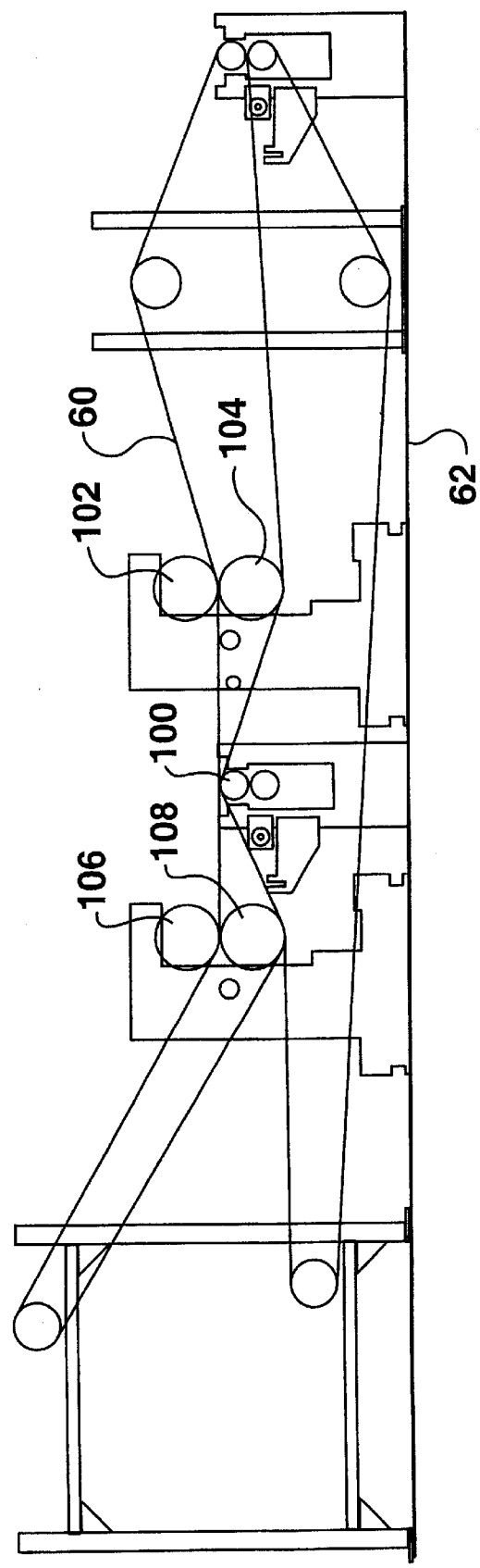
FIG. 6 is a schematic diagram of another alternative embodiment of a process for improving the tactile properties of a formed base web made in accordance with the present invention.
Figure 7:
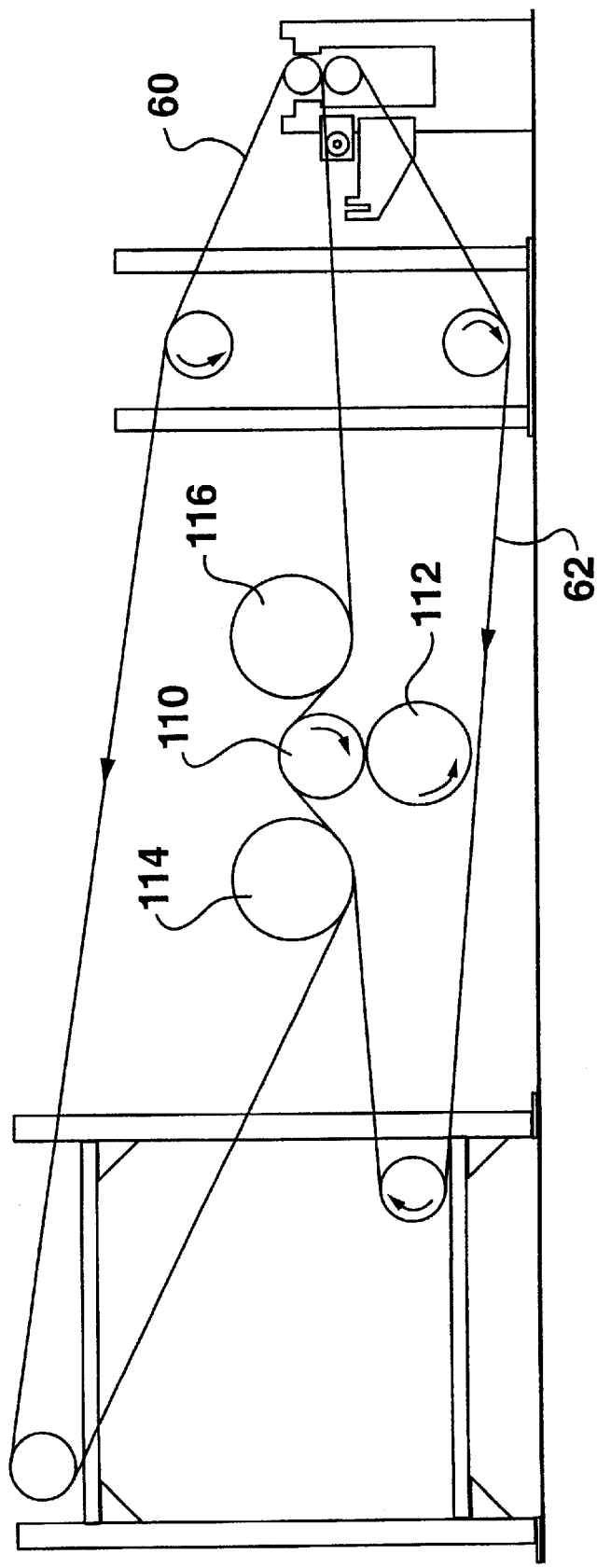
FIG. 7 is a schematic diagram of a further alternative embodiment of a process for improving the tactile properties of a formed base web made in accordance with the present invention.

Further embodiments of systems made in accordance with the present invention are illustrated in FIGS. 6 and 7. The system illustrated in FIG. 6 includes a single shear inducing roll 100. As shown, conveyors 60 and 62 are guided around the shear inducing roll 100 by support rolls 102, 104, 106 and 108.

The system illustrated in FIG. 7 also includes a single shear inducing roll 110. It should be understood, however, that more shear inducing rolls can be included in any of the systems illustrated. As shown in FIG. 7, shear inducing roll 110 is supported by a backing roll 112. In order to facilitate the amount of wrap around shear inducing roll 110, the system further includes support rolls 114 and 116.

As stated above, base webs processed according to the present invention can be made from various materials and fibers. For instance, the base web can be made from pulp fibers, other natural fibers, synthetic fibers, and the like.

For instance, in one embodiment of the present invention, the base web contains pulp fibers either alone or in combination with other types of fibers. The pulp fibers used in forming the web can be, for instance, softwood fibers having an average fiber length of greater than 1 mm and particularly from about 2 to 5 mm based on a length weighted average. Such fibers can include Northern softwood kraft fibers. Secondary fibers obtained from recycled materials may also be used.

In one embodiment, staple fibers (and filaments) can be added to the web to increase the strength, bulk, softness and smoothness of the web. Staple fibers can include, for instance, polyolefin fibers, polyester fibers, nylon fibers, polyvinyl acetate fibers, cotton fibers, rayon fibers, non-woody plant fibers, and mixtures thereof. In general, staple fibers are typically longer than pulp fibers. For instance, staple fibers typically have fiber lengths of 5 mm and greater.

The staple fibers added to the base web can also include bicomponent fibers. Bicomponent fibers are fibers that can contain two materials such as but not limited to in a side by side arrangement or in a core and sheath arrangement. In a core and sheath fiber, generally the sheath polymer has a lower melting temperature than the core polymer. For instance, the core polymer, in one embodiment, can be nylon or a polyester, while the sheath polymer can be a polyolefin such as polyethylene or polypropylene. Such commercially available bicomponent fibers include CELBOND fibers marketed by the Hoechst Celanese Company.

The staple fibers used in the base web of the present invention can also be curled or crimped. The fibers can be curled or crimped, for instance, by adding a chemical agent to the fibers or subjecting the fibers to a mechanical process. Curled or crimped fibers may create more entanglement and void volume within the web and further increase the amount of fibers oriented in the Z direction as well as increase web strength properties.

In one embodiment, when forming paper products containing pulp fibers, the staple fibers can be added to the web in an amount from about 5% to about 30% by weight and particularly from about 5% to about 20% by weight.

When the base web of the present invention is not used to make paper products, but instead is incorporated into other products such as diapers, feminine hygiene products, garments, personal care products, and various other products, the base web can be made from greater amounts of staple fibers.

Besides pulp fibers and staple fibers, thermomechanical pulp can also be added to the base web. Thermomechanical pulp, as is known to one skilled in the art, refers to pulp that is not cooked during the pulping process to the same extent as conventional pulps. Thermomechanical pulp tends to contain stiff fibers and has higher levels of lignin. Thermomechanical pulp can be added to the base web of the present invention in order to create an open pore structure, thus increasing bulk and absorbency and improving resistance to wet collapse.

When present, the thermomechanical pulp can be added to the base web in an amount from about 10% to about 30% by weight. When using thermomechanical pulp, a wetting agent is also preferably added during formation of the web. The wetting agent can be added in an amount less than about 1% and, in one embodiment, can be a sulphonated glycol.

In some embodiments, it is desirable to limit the amount of inner fiber-to-fiber bond strength. In this regard, the fiber furnish used to form the base web can be treated with a chemical debonding agent. The debonding agent can be added to the fiber slurry during the pulping process or can be added directly into the headbox. The amount of debonding agent added to the fibers depends upon the particular application. For instance, the debonding agent can be contacted with the fibers in an amount from about 0.1% to about 10% by weight, particularly from about 0.1% to 5% by weight, and more particularly from about 0.1% to about 1% by weight, based upon the total weight of fibers.

Suitable debonding agents that may be used in the present invention include cationic debonding agents such as fatty dialkyl quaternary amine salts, mono fatty alkyl tertiary amine salts, primary amine salts, imidazoline quaternary salts, and unsaturated fatty alkyl amine salts. Other suitable debonding agents are disclosed in U.S. Pat. No. 5,529,665 to Kaun which is incorporated herein by reference.

In one embodiment, the debonding agent used in the process of the present invention can be an organic quaternary ammonium chloride. In this embodiment, the debonding agent can be added to the fiber slurry in an amount from about 0.1% to about 1% by weight, based on the total weight of fibers present within the slurry.

The base web of the present invention may also have a multi-layer construction. For instance, the web can be made from a stratified fiber furnish having at least three principal layers.

It has been discovered by the present inventors that various unique products can be formed when processing a stratified base web according to the present invention. For example, as described above, the process of the present invention causes web disruption in the area of the web that is weakest. Consequently, one particular embodiment of the present invention is directed to using a stratified base web that contains weak outer layers and a strong center layer. Upon exposure to the shear forces created through the process of the present invention, bonds are broken on the outer surface of the sheet, while the strength of the center layer is maintained. The net effect is a base web having improved softness and stiffness with minimal strength loss.

In an alternative embodiment, a stratified base web can be formed that has outer layers having a greater tensile strength and/or shear strength than a middle layer. In this embodiment, upon exposure to the shear forces created by the process of the present invention, bonds in the middle layer can fail but the integrity of the outer layers can be maintained. The resulting sheet simulates, in some respects, the properties of a two-ply sheet.

Alternatively, in other embodiments, the layers of the stratified base web need not necessarily be of equal construction to each other. It may be desirable to have all layers of different construction and/or tensile strengths.

There are various methods available for creating stratified base webs. For instance, referring to FIG. 1, one embodiment of a device for forming a multi-layered stratified fiber furnish is illustrated. As shown, a three-layered headbox generally 10 may include an upper headbox wall 12 and a lower headbox wall 14. Headbox 10 may further include a first divider 16 and a second divider 18, which separate three fiber stock layers. Each of the fiber layers 24, 20, and 22 comprise a dilute aqueous suspension of fibers.

An endless traveling forming fabric 26, suitably supported and driven by rolls 28 and 30, receives the layered stock issuing from headbox 10. Once retained on fabric 26, the layered fiber suspension passes water through the fabric as shown by the arrows 32. Water removal is achieved by combinations of gravity, centrifugal force and vacuum suction depending on the forming configuration.

Forming multi-layered webs is also described and disclosed in U.S. Pat. No. 5,129,988 to Farrington, Jr. and in U.S. Pat. No. 5,494,554 to Edwards, et al., which are both incorporated herein by reference.

In forming stratified base webs, various methods and techniques are available for creating layers that have different shear strengths and/or tensile strengths. For example, debonding agents can be used as described above in order to alter the strength of a particular layer.

Alternatively, different fiber furnishes can be used for each layer in order to create a layer with desired characteristics. For example, in one embodiment, softwood fibers can be incorporated into a layer for providing strength, while hardwood fibers can be incorporated into an adjacent layer for creating a weaker layer.

More particularly, it is known that layers containing hardwood fibers typically have a lower tensile and shear strength than layers containing softwood fibers. Hardwood fibers have a relatively short fiber length. For instance, hardwood fibers can have a length of less than about 2 millimeters and particularly less than about 1.5 millimeters.

In one embodiment, the hardwood fibers incorporated into a layer of the base web include eucalyptus fibers. Eucalyptus fibers typically have a length of from about 0.8 millimeters to about 1.2 millimeters. When added to the web, eucalyptus fibers increase the softness, enhance the brightness, increase the opacity, and increase the wicking ability of the web.

Besides eucalyptus fibers, other hardwood fibers may also be incorporated into the base web of the present invention. Such fibers include, for instance, maple fibers, birch fibers and possibly recycled hardwood fibers.

In general, the above-described hardwood fibers can be present in the base web in any suitable amount. For example, the fibers can comprise from about 5% to about 100% by weight of one layer of the web.

The hardwood fibers can be present within the lower tensile strength layer of the web either alone or in combination with other fibers, such as other cellulosic fibers. For instance, the hardwood fibers can be combined with softwood fibers, with super absorbent materials, and with thermomechanical pulp.

Besides hardwood fibers, in other embodiments, a relatively weak layer can be created using synthetic fibers. In particular, synthetic fibers do not form bonds between themselves such as cellulosic fibers and therefore may be used to form weaker layers.

In still another alternative embodiment of the present invention, a weaker layer can be formed using debonded fibers. Debonded fibers refer to fibers treated with a debonding agent as described above.

In addition to the above-described hardwood fibers, other fibers particularly well-suited for use in the lower tensile strength and/or lower shear strength layer of the base web are cellulose fibers which have been permanently curled or stiffened in order to decrease bonding. As used herein, permanently curled fibers are fibers which have been subjected to any of several possible processes to increase total curvature along a length of the fiber, and stiffened fibers are those which have been treated in order that the fibers exhibit a lower bending stiffness.

One possible method to produce permanently curled cellulose fibers or stiffened fibers is a mercerization process wherein cellulosic fibers are treated with an alkali, typically sodium hydroxide, to convert the cellulose into a more thermodynamically stable, less crystalline form. Quenching the alkali while the fibers are distorted stabilizes the new shape at a lower pH value.

Another method for permanently curling and stiffening cellulosic fibers is by chemically cross-linking. This treatment is performed by adding a chemical cross-linking agent to either a solution containing lignocellulosic fibers or directly to the swollen cellulosic fibers themselves. Some examples of cross-linking agents that can be used can include polycarboxylic acids, glycols, formaldehyde agents, and the like. The fibers are then dried and cured in a predominately individualized form to promote intra-fiber cross links. This stabilizes the fiber in a highly twisted state.

Additionally, cross-linking increases the stiffness of the fiber through increased intra-fiber bonding.

Yet another possible method for producing permanently curled or stiffened cellulosic fibers is by mechanical means. When lignocellulosic fibers are mechanically treated by being subjected to a high shear force and/or high temperatures, the fibers will be twisted into distorted, curled shapes. Lignin containing fibers are especially susceptible to being curled in this fashion due to the lower glass transition temperature of lignin.

In another embodiment of the present invention, stiffened fibers are produced through thermal modification. In particular, cellulosic fibers are heated to temperatures that create aldehyde groups that cross-link causing the fibers to stiffen. This process is sometimes referred to as hornification.

For most applications, the permanently curled or stiffened cellulose fibers are contained in a middle layer of a base web processed according to the present invention for creating a relatively weak center layer. The permanently curled or stiffened cellulose fibers can be contained within a middle layer either alone or in conjunction with other fibers, such as hardwood fibers.

Alternatively, it may be desirable to include in the weak center layer non-bonding synthetic fibers. Non-bonding synthetic fibers may be well suited for inclusion in the weak center layer due to the lack of H-bonding associated with synthetic fibers.

The outside layers of the base web, for most applications, should have a tensile strength and/or shear strength greater than the middle layer containing the permanently curled cellulose fibers. For example, the outer layers of the web can be made from pure or blends of softwood fibers, hardwood fibers, broke, or mechanical pulps. In one further embodiment, the outside layers can contain any of the above-described fibers in combination with staple fibers, such as synthetic fibers.

The weight of each layer of a stratified base web in relation to the total weight of the web is generally not critical. In most embodiments, however, the weight of each outer layer will be from about 12.5% to about 40% of the total weight of the web, and particularly from about 25% to about 35% of the weight of the web.

One method of quantifying the characteristics of a web (such as one layer of a stratified web) is by measuring the shear strength. Shear strength is the maximum stress a material may withstand without rupture, the stress being applied in a direction parallel with the surface of the material. As described herein, shear strength may be determined by the following method:

A sample of a web (which can represent one layer of a web) is first conditioned under TAPPI conditions (50% relative humidity and 73° F.) for four hours. The sample is then trimmed to a piece two inches in length (machine direction) by one inch width (cross direction).

A five inch piece of Scotch®810D tape is applied to one side of the sample, such that one end of the tape is even with one end of the sample and three inches of the tape extend beyond the other end of the sample. The three inch tape extension is then folded over on itself to create a 1½ inch double tape "handle" extending beyond the end of the sample. This same process is repeated with another piece of tape on the other side of the sample with the tape handle of the second side extending in the opposite direction off of the sample from the first tape handle. The tape should be firmly affixed to both sides of the sample with pressure. The sample is then trimmed to the width of the tape, so the final sample for testing is two inches long (machine direction) by 0.75 inches wide (cross direction) with tape "handles" extending 1½ inches beyond either end.

The sample is installed into an MTS Synergie Tensile Test Frame with two inch wide handsheet style grips. The span between the grips is four inches, and the grips are attached to the tape handles at either end of the sample.

The specimen is elongated at a rate of 0.5 in/min until failure. The specimen must be examined after failure to be sure the sample is still firmly attached to both pieces of the tape. If not, the tape, rather than the specimen has failed and the sample must be discarded.

The load at failure is the maximum load. The shear strength in Pa is determined as:

$$\text{Shear strength} = \frac{\text{Maximum load (in Newtons)}}{\text{Area of sample in m}^2}$$

The desired shear strength of a base web depends on the final product. For a bath tissue product shear strength can be less than 10 kPa, particularly less than 5 kPa, more particularly less than 2 kPa. For a towel product, shear strength can be less than 20 kPa, particularly less than 15 kPa, more particularly less than 10 kPa.

Besides shear strength, tensile strength may also be an important property to measure in stratified webs made according to the present invention. A process for measuring the tensile strength of a web is described in the example which follows.

The basis weight of base webs made according to the present invention can vary depending upon the particular application. In general, for most applications, the basis weight can be from about 5 pounds per 2,880 square feet (ream) to about 80 pounds per ream, and particularly from about 6 pounds per ream to about 30 pounds per ream. Some of the uses of the base webs include use as a wiping product, as a napkin, as a medical pad, as an absorbent layer in a laminate product, as a placemat, as a drop cloth, as a cover material, as a facial tissue, as a bath tissue, or for any product that requires liquid absorbency.

The present invention may be better understood with reference to the following examples.

EXAMPLE

The following example was conducted in order to illustrate the advantages and benefits of the present invention.

In this experiment, paper webs were produced, placed between two fabrics, and then guided around at least one shear inducing roll. More particularly, stratified webs were tested which included three layers. The two outer layers of the web were made from eucalyptus fibers. The middle layer, however, contained softwood fibers. The webs were produced using a through air dryer similar to the system illustrated in FIG. 3. The base webs had an average basis weight of about 18.9 lbs/ream.

Once formed, the webs were then placed in between a pair of fabrics and guided around at least one shear inducing roll, similar to the configuration illustrated in FIG. 4.

In the first set of experiments, the base web and fabric sandwich was wrapped around 3 shear inducing rolls at a pressure of 25 pounds per linear inch. The fabrics were wrapped around the shear inducing rolls in an amount of about 45°.

During the first set of tests, the diameter of the shear inducing rolls was varied between 2 inches, 4.5 inches and 10.5 inches. Further, the amount of softwood fibers contained in the web was also varied (middle layer of the web) from 28% by weight to 31% by weight.

Figure 8:
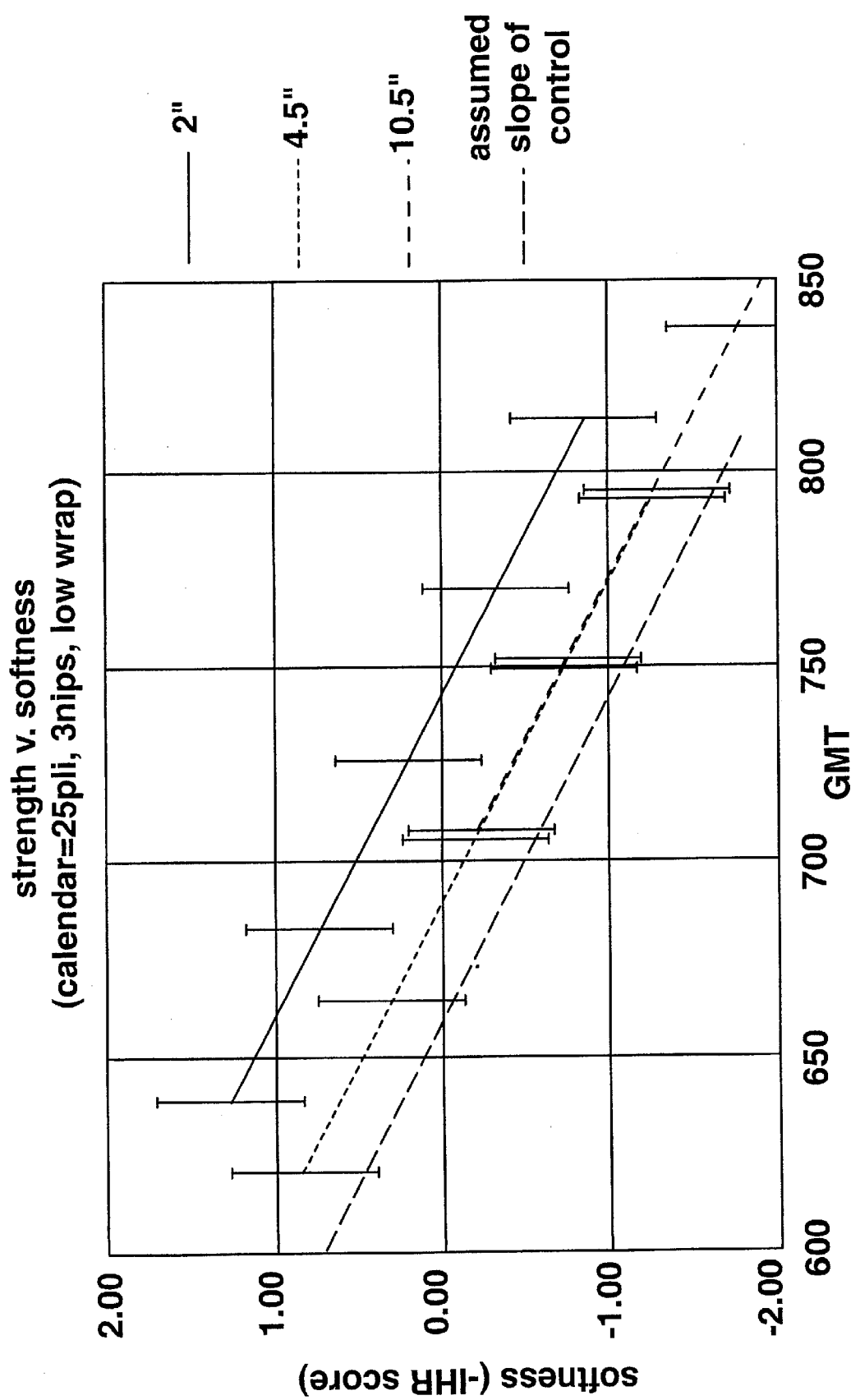
FIGS. 8 and 9 are the results obtained in the example described below.

Linear regression mathematical models were developed for strength and softness in order to create strength and softness curves. The results of the first set of experiments is illustrated in FIG. 8. For purposes of comparison, a control curve was also created. The control curve was produced by calendering the base web at a pressure of 150 pounds per linear inch, instead of subjecting the web to the shear inducing rolls and then estimating a curve.

During these tests, softness was determined using an in hand ranking test (IHR). Panelists received 6 samples and were asked to rank them for softness based upon subjective criteria. Specifically, the panelists received different sets of samples several times. Each sample was coded. Replicates were compared in order to estimate error. The panelists' response data was modeled with Logistic Regression to determine paired scores and log odds.

Strength was determined using a geometric mean tensile strength test (GMT). In particular, the tensile strength of samples was determined in the machine direction and in the cross machine direction. During the test, each end of a sample was placed in an opposing clamp. The clamps held the material in the same plane and moved apart at a ten inch per minute rate of extension. The clamps moved apart until breakage occurred in order to measure the breaking strength of the sample. The geometric mean tensile strength is then calculated by taking the square root of the machine direction tensile strength of the sample multiplied by the cross direction tensile strength of the sample.

In order to construct the graph illustrated in FIG. 8, linear regression models were calculated for strength and softness. Specifically, a Y=f (x) model for strength and softness was created. A spreadsheet was created listing softness and strength values as the percent of softwood in the web varied for each of the three roll diameters of interest (2 inches, 4.5 inches, and 10.5 inches). For each point in the spreadsheet a value for strength and softness was calculated from the regression models. The graph shown in FIG. 8 was then created plotting softness on one axis and strength on the other axis grouped by the roll diameter.

As shown in FIG. 8 the process of the present invention shifts the strength/softness curve towards creating softer and stronger webs. Further, decreasing the shear inducing roll diameter further increases the softness of the webs at a given strength.

During the experiments, it was also noticed that between 5% to 15% caliper reduction was obtained, without positively or negatively affecting any product attributes.

Figure 9:
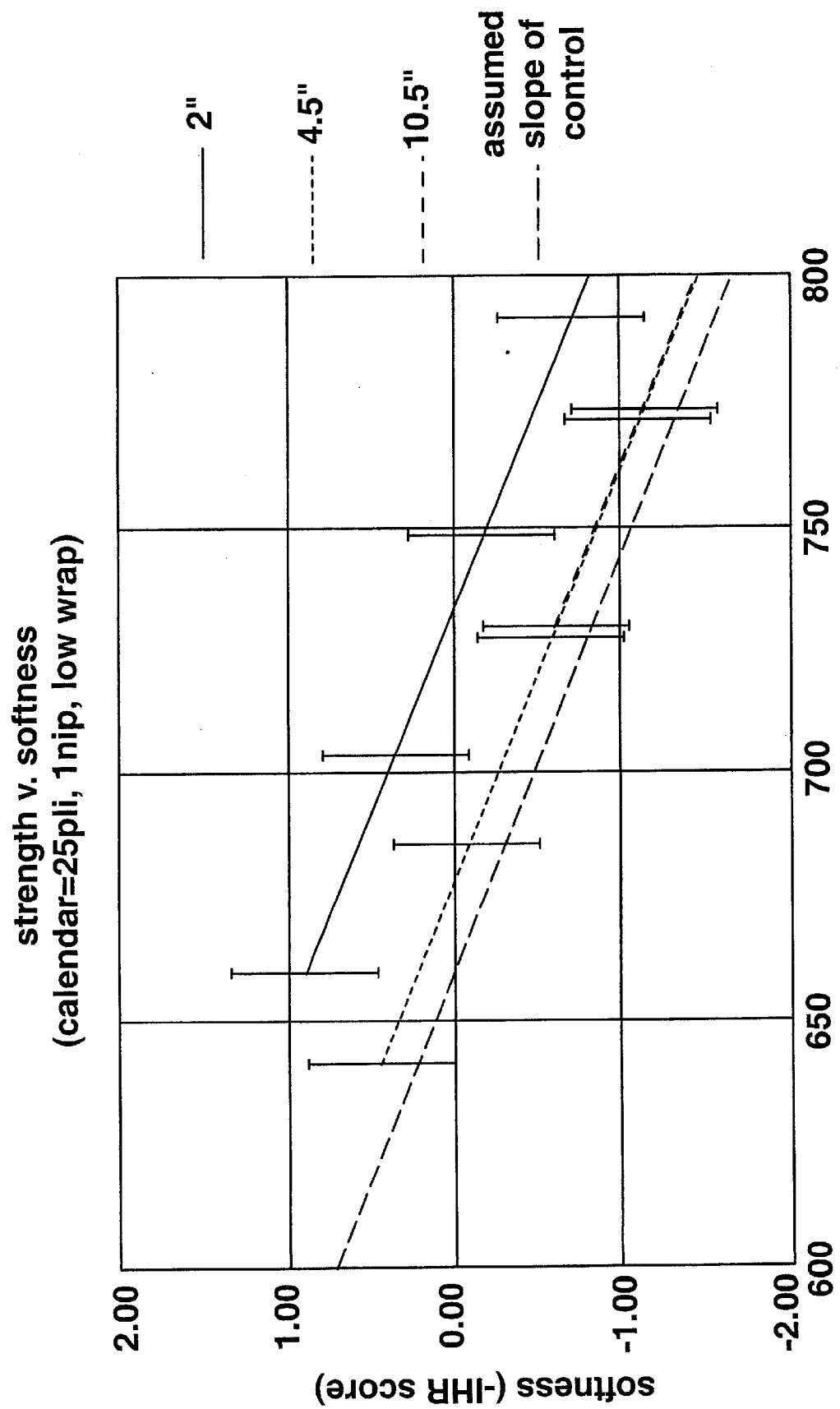

Using the mathematical models, another set of curves was generated from another set of experiments. Specifically, in this set of experiments, only a single shear inducing roll was used. The results are shown in FIG. 9.

As shown, a decrease in the diameter of the shear inducing roll had a greater impact upon the base webs in comparison to the control.

These and other modifications and variations to the present invention may be practiced by those of ordinary skill in the art, without departing from the spirit and scope of the present invention, which is more particularly set forth in the appended claims. In addition, it should be understood that aspects of the various embodiments may be interchanged both in whole or in part. Furthermore, those of ordinary skill in the art will appreciate that the foregoing description is by way of example only, and is not intended to limit the invention so further described in such appended claims.

What is claimed is:

1. A process for producing base webs comprising the steps of:
    forming a stratified base web containing pulp fibers, said base web including a middle layer positioned in between a first outer layer and a second outer layer, said first and second outer layers having a greater shear strength than said middle layer, said middle layer containing cellulose fibers which have been stiffened;
    placing said base web in between a first moving conveyor and a second moving conveyor, the base web having a moisture content of about 10% or less; and
    guiding said first moving conveyor and said second moving conveyor around a shear inducing roll while said base web is positioned in between said conveyors.

2. A process as defined in claim 1, wherein said shear inducing roll has a diameter of less than about 10 inches.

3. A process as defined in claim 1, wherein said stiffened cellulosic fibers comprise thermally modified fibers.

4. A process as defined in claim 1, wherein said first moving conveyor and said second moving conveyor are guided around at least two shear inducing rolls.

5. A process as defined in claim 1, wherein said base web has a basis weight of from about 5 pounds per ream to about 90 pounds per ream.

6. A process as defined in claim 1, wherein said first moving conveyor and said second moving conveyor are under a tension of at least 5 pounds per linear inch when guided around said shear inducing roll.

7. A process as defined in claim 1, wherein said cellulose fibers mercerized fibers.

8. A process as defined in claim 1, wherein said cellulose fibers comprise cross-linked fibers.

9. A process as defined in claim 1, wherein said first outer layer and said second outer layer comprise softwood fibers.

10. A process for producing base webs comprising the steps of:
    forming a stratified base web including a middle layer positioned in between a first outer layer and second outer layer, said first and second outer layers having a greater shear strength than said middle layer, said middle layer containing mercerized fibers;
    placing said base web in between a first moving conveyor and a second moving conveyor, the base web having a moisture content of about 10% or less;
    guiding said first moving conveyor and said second moving conveyor around at least one shear inducing roll while said base web is positioned in between said conveyors, said first and second conveyors being wrapped around said at least one shear inducing roll at least about 40° and being placed under a sufficient amount of tension around said shear inducing roll so as to create shear forces that act upon the base web.

11. A process as defined in claim 10, wherein said first and second conveyors are wrapped around at least 2 shear inducing rolls.

12. A process as defined in claim 10, wherein said first and second conveyors are wrapped around at least 3 shear inducing rolls.

13. A process as defined in claim 10, wherein said first and second conveyors are wrapped around at least 5 shear inducing rolls.

14. A process as defined in claim 10, wherein said first and second conveyors are under tension in an amount from about 10 pounds per linear inch to about 50 pounds per linear inch when guided around said at least one shear inducing roll.

15. A process as defined in claim 10, wherein said shear inducing roll has a diameter of less than about 7 inches.

16. A process as defined in claim 10, wherein said middle layer comprises from about 12.5% to about 40% of the total weight of the web.

17. A process as defined in claim 10, wherein said first and second outer layers contain softwood fibers.

18. A process for producing base webs comprising the steps of:

forming a stratified base web, said stratified base web containing a middle layer positioned in between a first outer layer and a second outer layer, said first and second outer layers having a greater shear strength than said middle layer, said middle layer containing stiffened cellulose fibers;

placing said base web in between a first moving conveyor and a second moving conveyor;

guiding said first moving conveyor and said second moving conveyor around at least one shear inducing roll while said base web is positioned in between said conveyors and while said base web has a moisture content of less than 10% by weight, said at least one shear inducing roll having a diameter of less than about 7 inches, said first and second conveyors being wrapped around said at least one shear inducing roll at least 80°.

19. A process as defined in claim 18, wherein said first conveyor and said second conveyor are guided around at least 2 shear inducing rolls, said conveyors being wrapped around each of said shear inducing rolls at least 80°.

20. A process as defined in claim 18, wherein said at least one shear inducing roll has a diameter of from about 2 inches to about 5 inches and wherein said first and second conveyors are wrapped around said shear inducing roll at least 100°.

21. A process as defined in claim 18, wherein said first and second conveyors are under tension in an amount of at least 30 pounds per linear inch when wrapped around said at least one shear inducing roll.

22. A process as defined in claim 18, wherein said first and second outer layers contain softwood fibers.

23. A process as defined in claim 18, wherein said middle layer contains mercerized fibers.

24. A process as defined in claim 18, wherein said middle layer contains cross-linked fibers.

25. A process as defined in claim 18, wherein said stiffened cellulose fibers comprise thermally modified fibers.

26. A process as defined in claim 18, wherein said middle layer comprises from about 25% to about 35% of the weight of the web.

27. A process as defined in claim 18, wherein said base web comprises a tissue product.

28. A process as defined in claim 18, wherein said stratified base web has a basis weight of less than about 25 lbs per ream.

29. A process for producing base webs comprising the steps of:

forming a stratified base web including a middle layer positioned in between a first outer layer and a second outer layer, said first and second outer layers having a greater shear strength than said middle layer, said middle layer containing debonded fibers;

placing said base web in between a first moving conveyor and a second moving conveyor, the base web having a moisture content of about 10% or less;

guiding said first moving conveyor and said second moving conveyor around at least one shear inducing roll while said base web is positioned in between said conveyors, said first and second conveyors being wrapped around said at least one shear inducing roll at least about 40° and being placed under a sufficient amount of tension around said shear inducing roll so as to create shear forces that act upon the base web.

30. A process as defined in claim 29, wherein said first and second conveyors are wrapped around at least 2 shear inducing rolls.

31. A process as defined in claim 29, wherein said first and second conveyors are wrapped around at least 3 shear inducing rolls.

32. A process as defined in claim 29, wherein said first and second conveyors are wrapped around at least 5 shear inducing rolls.

33. A process as defined in claim 29, wherein said first and second conveyors are under tension in an amount from about 10 pounds per linear inch to about 50 pounds per linear inch when guided around said at least one shear inducing roll.

34. A process as defined in claim 29, wherein said shear inducing roll has a diameter of less than about 7 inches.

35. A process as defined in claim 29, wherein said middle layer comprises from about 12.5% to about 40% of the total weight of the web.

36. A process as defined in claim 29, wherein said first and second outer layers contain softwood fibers.

37. A process as defined in claim 29, wherein said debonded fibers comprise fibers that have been contacted with a chemical debonding agent.

38. A process as defined in claim 37, wherein the debonding agent is contacted with the fibers in an aqueous slurry, the debonding agent being present in the slurry in an amount from about 0.1% to about 10% by weight, based on the total weight of fibers present within the slurry.

39. A process as defined in claim 37, wherein the debonding agent is contacted with the fibers in an aqueous slurry, the debonding agent being present in the slurry in an amount from about 0.1% to about 5% by weight, based on the total weight of fibers present within the slurry.

40. A process as defined in claim 37, wherein the debonding agent is contacted with the fibers in an aqueous slurry, the debonding agent being present in the slurry in an amount from about 0.1% to about 1% by weight, based on the total weight of fibers present within the slurry.

41. A process as defined in claim 37, wherein the debonding agent comprises a quaternary ammonium salt.

* * * * *